US008691989B2

(12) United States Patent
Lawson

(10) Patent No.: US 8,691,989 B2
(45) Date of Patent: Apr. 8, 2014

(54) METHODS OF SYNTHESIS OF MORPHINANS

(75) Inventor: John A. Lawson, Hyde Park, UT (US)

(73) Assignee: Phoenix Pharmalabs, Inc., Hyde Park, UT (US)

( * ) Notice: Subject to any disclaimer, the term of this patent is extended or adjusted under 35 U.S.C. 154(b) by 1268 days.

(21) Appl. No.: 12/143,608

(22) Filed: Jun. 20, 2008

(65) Prior Publication Data

US 2009/0318699 A1  Dec. 24, 2009

(51) Int. Cl.
*C07D 489/02* (2006.01)
*C07D 489/00* (2006.01)

(52) U.S. Cl.
USPC ............................................. 546/46; 546/44

(58) Field of Classification Search
USPC ....................................... 546/46, 44
See application file for complete search history.

(56) References Cited

U.S. PATENT DOCUMENTS

| | | |
|---|---|---|
| 3,342,824 A | 9/1967 | Pohland et al. |
| 4,218,454 A | 8/1980 | DeGraw et al. |
| 4,749,706 A | 6/1988 | Lawson et al. |

FOREIGN PATENT DOCUMENTS

| | | |
|---|---|---|
| DE | 2254298 A1 | 5/1974 |
| WO | 8705903 A2 | 10/1987 |
| WO | 9118606 A2 | 12/1991 |
| WO | WO 91/18606 | 12/1991 |

OTHER PUBLICATIONS

Bentley et al. (1967) "Novel analgesics and molecular rearrangements in the morphine-thebaine group. III. Alcohols of the 6,14-endo-ethenotetrahydrooripavine series and derived analogs of N-allylnormorphine and -norcodeine," *J Am. Chem. Soc.* 89:3281-3292.
Jacobson et al. (1979) "Paradoxical effects of N-cyanoalkyl substituents upon the activities of several classes of opioids" *J. Med. Chem.* 22:328-331.
Coop et al. (2000) "Structural determinants of opioid activity in the orvinols and related structures: ethers of orvinol and isoorvinol," *J. Med. Chem.* 43(9):1852-1857.
PCT International Search Report dated Aug. 21, 2009.
Cooper et al., (1985) "Synthesis of N-p-Azidophenylethyl-7,8-Dihydronormorphine and its 7,8-Ditritio Analogue. Potential Opiate Receptor Photoaffinity Labels" *Journal of Labelled Compounds and Radiopharmaceuticals*, vol. XXII, No. 11, 1201-1207.
Gates et al., (1989) "Derivatives of the Thebaine Anion. 2. 5-Methylmorphine, 5-Methylcodeine, 5-Methylheroin, and Some Related Compounds" *J. Org. Chem.* 54:972-974.
Hosztafi et al., (1992) "Synthesis of N-Demethyl-N-Substituted Dihydroisomorphine and Dihydroisocodeine Derivatives" *Syn. Comm.*, 22(12):1673-1682.
May et al., (1966) "Interesting Pharmacological Properties of the Optical Isomers of α-5,9-Diethyl-2'-hydroxy-2-methyl-6,7-benzomorphan" *J. Med. Chem.*, 9(6):851-2.
International Preliminary Report on Patentability for International Application No. PCT/US2009/002875; International Filing Date: May 8, 2009; Date of Mailing: Dec. 21, 2010; 9 Pages.
Written Opinion of the International Searching Authority of International Application No. PCT/US2009/002875; International Filing Date: May 8, 2009; Date of Mailing: Dec. 20, 2010. 8 Pages.
International Search Report of the International Searching Authority of International Application No. PCT/US2009/002875; International Filing Date: May 8, 2009; Date of Mailing: Dec. 23, 2010. 4 Pages.
You et al. "Research and Application of Chiral Drugs" Asymmetric Organic Synthesis-Drug Chemical IV.R914.5. China Library CIP Shujuhezi (2003) No. 059450, Beijing Chemical Industry Press, Jul. 2003.
Berenyi et al., "Preparation of Demethoxyoripavine and its Conversion into N-Substituted N-Demethylapomorphine Derivatives"; Acta Cimica Hungarica; 113 (1); (1983); pp. 51-60.
Dong et al., "New Methodology for the N-Demethylation of Opiate Alkaloids"; Journal of Organic Chemistry; 68(25); (2003); pp. 9847-9850.
Hosztafi et al., "N-Demethylation of Morphine Alkaloids. Preparation of Norneopine", Acta Cimica Academiae Scientiarum Hungaricae; 103(4); (1980); pp. 371-375.
Mccamley et al., "Efficient N-Demethylation of Opiate Alkaloids Using a Modified Nonclassical Polonovski Reaction"; Journal of Organic Chemistry; 68; (2003); pp. 9847-9850.
Thavaneswaran et al., "Further Investigation of the N-Demethylation of Tertiary Amine Alkaloids Using the Non-Classical Polonovski Reaction"; Bioorganic and Medicinal Chemistry Letters; 16(11); (2006); pp. 2868-2871.

*Primary Examiner* — Charanjit Aulakh
(74) *Attorney, Agent, or Firm* — Cantor Colburn LLP

(57) ABSTRACT

The disclosure describes morphinan compounds and methods for their synthesis. Preferred methods according to the disclosure allow for large-scale preparation of diastereomerically enriched morphinans. Preferred methods according to the disclosure may also allow for the preparation of diastereomerically enriched morphinans using less time, and/or using fewer reaction steps, and/or providing better yield than previously used methods for preparing morphinans. The methods disclosed herein find utility in synthetic organic chemistry as well as medicinal chemistry.

30 Claims, No Drawings

METHODS OF SYNTHESIS OF MORPHINANS

TECHNICAL FIELD

This disclosure relates generally to methods suitable for synthesizing morphinan compounds. The invention finds utility, for example, in the fields of synthetic organic chemistry and pharmaceutical science.

BACKGROUND

Morphinans are compounds based on the core chemical structure

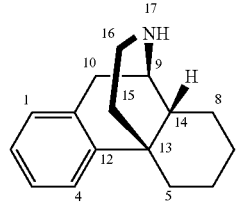

A common example of a morphinan is morphine, a widely used and powerful analgesic. Morphine is an opioid that binds to opioid receptors in the central nervous system. However, the drug has serious side effects that present severe clinical problems, including drug dependence, suppression of respiration and suppression of smooth muscle movement. Alternative morphinan analogs have been studied and investigated in a search for compounds that shares the benefits of morphine with fewer negative side effects.

U.S. Pat. No. 4,218,454 to DeGraw et al. discloses morphinan analogs having the formula

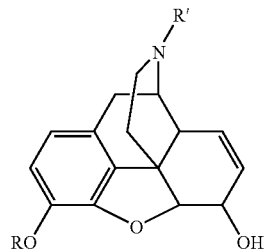

wherein R is hydrogen or methyl and R' is selected from various alkyl and alkene groups with a CH chiral moiety directly attached to N. The compounds are prepared using codeine as a starting material. In a typical synthesis, codeine is converted to norcodeine in two reaction steps. The norcodeine product is n-alkylated using lactonitrile, and the lactonitrile adduct is converted to the target morphinan analog in a two step procedure using first a Grignard reagent to transform a nitrile group to a cyclopropane group followed by diphenyphosphide to convert R from methyl to hydrogen. The compounds prepared using this method are reported to have strong agonist potency, moderate antagonist qualities, and low addiction potential.

U.S. Pat. No. 4,749,706 to Lawson et al. discloses morphinan analogs having the formula

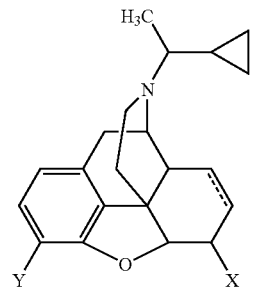

wherein Y is OH or OMe; the dotted line indicates the presence or absence of a π bond; X is —OH or =O. The absolute configuration of the α-carbon (i.e., the carbon attached to the nitrogen atom and the cyclopropane group) is not disclosed. The compounds are prepared using morphine as a starting material. In a typical synthesis, morphine is converted to normorphine in two reaction steps. The normorphine product is N-alkylated using sodium cyanoborohydride ($NaCNBH_3$). The resulting mixture of diastereomers is reacted with benzoyl chloride to form the dibenzoate ester, and then separated using preparative HPLC. Removal of the benzoate esters affords the final product. The compounds prepared by this method are reported to be highly active analgesics and to have minimal addicting capability.

The synthetic methods described in the above-mentioned US patents involve numerous reaction steps and often produce low yields [<5%]. In addition, while the methods may be suitable for laboratory-scale preparations, scale-up of the methods for large-scale preparations is fraught with practical difficulties.

Beyond the US patents mentioned above, N-demethylations of morphine have been conducted utilizing toxic agents such as cyanogen bromide, ACE-Cl, and methyl chloroformate. These reagents lead to N—CN or N-carbamates which require various conditions which are laborious in their work-up. For example, the intermediate from treatment with ACE-Cl requires long periods of reflux with powder zinc metal Previously, preparations of Buprenorphine and other orvinols were conducted including an N-demethylation step using methylazodicarboxylate as a mild oxidizing agent to convert the N-methyl to an aminal (see Bentley et al., (1967) *Journal of the American Chemical Society*, 89:13, 3281-3292). This method was reportedly not effective for opiates, having been tested on codeine and morphine.

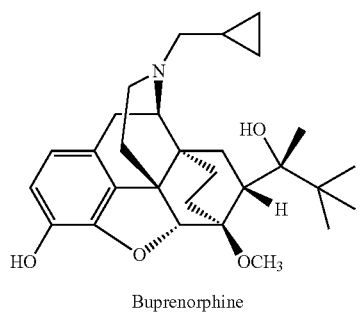 [SMILES: CO[C@]12CC[C@@]3(C[C@@H]1[C@](C)(O)C(C)(C)C)[C@H]1Cc4ccc(O)c5c4[C@@]3(CCN1CC1CC1)[C@H]2O5]

Buprenorphine

Furthermore, published methods for N-alkylation of opioids are associated with a variety of difficulties. In the methods described in U.S. Pat. No. 4,749,706, NaCNBH$_3$ must be added in portions over 1 hour and the pH must be adjusted by dropwise addition of HOAc during the reaction. The reaction mixture is heterogeneous slurry, requiring vigorous stirring.

The present invention is directed at addressing one or more of the abovementioned drawbacks.

SUMMARY OF THE DISCLOSURE

The present disclosure describes morphinan compounds and methods for their synthesis. It is preferred that such methods allow for large-scale preparation of the morphinans.

In one embodiment, then, the disclosure describes a method for preparing a diastereomerically enriched morphinan. The method comprises: (a) providing morphine or an analog thereof; (b) converting one or more hydroxyl groups on the morphine to one or more ester groups, in an esterification reaction, to prepare an esterified product; (c) converting the N—methyl group on the esterified product to an N—H group, in a demethylation reaction, to prepare a demethylated product; (d) converting the N—H group on the demethylated product to an N-alkyl group, in an alkylation reaction, to prepare an alkylated product; and (e) purifying the alkylated product in a purification step.

In another embodiment, the disclosure describes an improved method for preparing a diastereomerically enriched morphinan. In the method, the improvement comprises contacting a diastereomeric mixture of the morphinan with a resolving agent to form a salt and selectively recrystallizing one of the morphinan isomers.

In another embodiment, the disclosure describes an improved method for preparing a diastereomerically enriched morphinan. In the method, the improvement comprises: (a) providing a diastereomer of a morphinan; (b) epimerizing the diastereomer of the morphinan to a mixture of r- and s-diastereomers; (c) contacting the result from (b) with a resolving agent such that one of the diastereomers selectively forms a salt with the resolving agent; and (d) recrystallizing the result from (c). In a preferred embodiment, the diastereomer of the morphinan provided in (a) is the s-diastereomer of the morphinan, and the salt of the r-diastereomer is selectively recrystallized in (d).

In another embodiment, the disclosure describes an improved method for preparing a diastereomerically enriched morphinan. In the method, the improvement comprises: (a) recovering the pure or enriched S-diastereomer of a morphinan; (b) epimerizing the S-diastereomer into about a 50-50 mixture of the R-diastereomer and the S-diastereomer of the morphinan; (c) contacting the result from (b) with a resolving agent; and (d) purifying the result from (c). The pure or enriched S-diastereomer of a morphinan may be recovered, for example, from the synthetic methods described herein where appropriate.

In another embodiment, the disclosure describes an improved method for preparing a diastereomerically enriched morphinan. In the method, the improvement comprises: contacting a diester derivative of morphine with a demethylation reagent under reaction conditions effective to N-demethylate the diester derivative of morphine. In a preferred embodiment, the method involves mild and non-toxic conditions

DETAILED DESCRIPTION OF THE INVENTION

Definitions and Nomenclature

Unless otherwise indicated, the disclosure is not limited to specific procedures, starting materials, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

In describing and claiming the present invention, the following terminology will be used in accordance with the definitions set out below.

As used herein, the phrases "for example," "for instance," "such as," or "including" are meant to introduce examples that further clarify more general subject matter. These examples are provided only as an aid for understanding the disclosure, and are not meant to be limiting in any fashion.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl"

and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—$N^+$≡$C^-$), cyanato (—O—C≡N), isocyanato (—O—$N^+$≡$C^-$), isothiocyanato (—S—C≡N), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—$PO_2$), and phosphino (—PH$_2$), mono- and di-(C$_1$-C$_{24}$ alkyl)-substituted phosphino, mono- and di-(C$_5$-C$_{20}$ aryl)-substituted phosphino; and the hydrocarbyl moieties C$_1$-C$_{24}$ alkyl (including C$_1$-C$_{18}$ alkyl, further including C$_1$-C$_{12}$ alkyl, and further including C$_1$-C$_6$ alkyl), C$_2$-C$_{24}$ alkenyl (including C$_2$-C$_{18}$ alkenyl, further including C$_2$-C$_{12}$ alkenyl, and further including C$_2$-C$_6$ alkenyl), C$_2$-C$_{24}$ alkynyl (including C$_2$-C$_{18}$ alkynyl, further including C$_2$-C$_{12}$ alkynyl, and further including C$_2$-C$_6$ alkynyl), C$_5$-C$_{30}$ aryl (including C$_5$-C$_{20}$ aryl, and further including C$_5$-C$_{12}$ aryl), and C$_6$-C$_{30}$ aralkyl (including C$_6$-C$_{20}$ aralkyl, and further including C$_6$-C$_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

By two moieties being "connected" is intended to include instances wherein the two moieties are directly bonded to each other, as well as instances wherein a linker moiety is present between the two moieties. Linker moieties may include groups such as heteroatoms, C$_1$-C$_{24}$ alkylene (including C$_1$-C$_{18}$ alkylene, further including C$_1$-C$_{12}$ alkylene, and further including C$_1$-C$_6$ alkylene), C$_2$-C$_{24}$ alkenylene (including C$_2$-C$_{18}$ alkenylene, further including C$_2$-C$_{12}$ alkenylene, and further including C$_2$-C$_6$ alkenylene), C$_2$-C$_{24}$ alkynylene (including C$_2$-C$_{18}$ alkynylene, further including C$_2$-C$_{12}$ alkynylene, and further including C$_2$-C$_6$ alkynylene), C$_5$-C$_{30}$ arylene (including C$_5$-C$_{20}$ arylene, and further including C$_5$-C$_{12}$ arylene), and C$_6$-C$_{30}$ aralkylene (including C$_6$-C$_{20}$ aralkylene, and further including C$_6$-C$_{12}$ aralkylene).

The term "enantioenriched" is used to indicate that, where a compound may exist as two or more enantiomers, one of the enantiomers is present in excess of the other(s). For example, where two enantiomers of a compound are possible, an enantioenriched sample may include greater than 50%, greater than 60%, greater than 70%, greater than 75%, greater than 80%, greater than 85%, greater than 90%, greater than 95%, or greater than 99% of one of the enantiomers. A process is "enantioenriching" or "enantioselective" when the process favors production of one enantiomer over production of another enantiomer. Similarly, the term "diastereomerically enriched" is used to indicate that, where a compound may exist as two or more diastereomers, one of the diastereomers is present in excess of the other(s). For example, where two diastereomers of a compound are possible, a diastereomerically enriched sample may include greater than 50%, greater than 60%, greater than 70%, greater than 75%, greater than 80%, greater than 85%, greater than 90%, greater than 95%, or greater than 99% of one of the diastereomers. A process is "diastereomerically enriching" or "diastereoselective" when the process favors production of one diastereomer over production of another diastereomer.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

In one embodiment of the disclosure, then, a method is provided for preparing a diastereomerically enriched morphinan wherein the method is suitable for large-scale preparation of the desired product.

The morphinan may have the structure of formula (I)

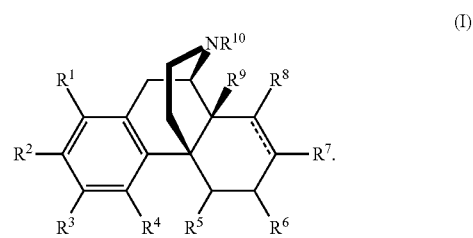

(I)

wherein, in formula (I):
the dashed line represents an optional double bond; and
R$^1$, R$^2$, R$^3$, R$^4$, R$^5$, R$^6$, R$^7$, R$^8$, R$^9$, and R$^{10}$ are independently selected from H, substituted or unsubstituted hydrocarbyl, substituted or unsubstituted heteroatom-containing hydrocarbyl, and functional groups.

For example, R$^1$, R$^2$, R$^3$, R$^4$, R$^5$, R$^6$, R$^7$, R$^8$, R$^9$, and R$^{10}$ may be H, substituted or unsubstituted C$_1$-C$_{12}$ alkyl, substituted or unsubstituted heteroatom-containing C$_1$-C$_{12}$ alkyl, substituted or unsubstituted C$_1$-C$_{12}$ alkenyl, substituted or unsubstituted heteroatom-containing C$_1$-C$_{12}$ alkenyl, substituted or unsubstituted C$_1$-C$_{12}$ alkynyl, substituted or unsubstituted heteroatom-containing C$_1$-C$_{12}$ alkynyl, substituted or unsubstituted C$_5$-C$_{24}$ aryl, substituted or unsubstituted C$_5$-C$_{24}$ heteroaryl, substituted or unsubstituted C$_5$-C$_{24}$ alkaryl, substituted or unsubstituted heteroatom-containing C$_5$-C$_{24}$ alkaryl, substituted or unsubstituted C$_5$-C$_{24}$ aralkyl, substituted or unsubstituted heteroatom-containing C$_5$-C$_{24}$ aralkyl, and functional groups. In addition, any two of R$^1$-R$^{10}$ may be linked to form a cyclic group, such that compounds of formula (I) may include one or more (e.g. 2, 3, or 4) annulated rings. Such rings may be independently selected from aromatic and alicyclic rings, and may be heterocyclic and/or further substituted with any of the substituents described herein. In one embodiment, any two of R$^1$-R$^{10}$ that are adjacent may be linked to form a cyclic group.

In a preferred embodiment of formula (I), the morphinan has the structure of formula (Ia)

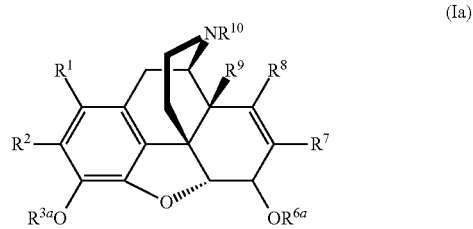

(Ia)

In formula (Ia), R$^1$, R$^2$, and R$^7$-R$^9$ are as described previously. R$^{3a}$ and R$^{6a}$ are independently selected from H, substituted or unsubstituted C$_1$-C$_{12}$ alkyl, substituted or unsubstituted C$_1$-C$_{12}$ alkenyl, substituted or unsubstituted C$_1$-C$_{12}$ alkynyl, substituted or unsubstituted C$_5$-C$_{24}$ aryl, substituted or unsubstituted C$_5$-C$_{24}$ alkaryl, substituted or unsubstituted C$_5$-C$_{24}$ aralkyl, and alcohol protecting groups.

In another preferred embodiment of formula (I), R$^1$, R$^2$, and R$^7$-R$^9$ are H, and the compounds have the structure of formula (Ib)

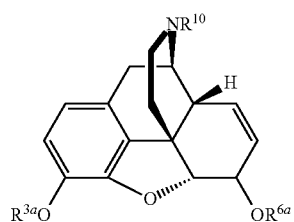

(Ib)

wherein $R^{3a}$, $R^{6a}$, and $R^{10}$ are as described previously. For example, $R^{3a}$ and $R^{6a}$ are hydrogen, and $R^{10}$ is selected from substituted or unsubstituted $C_1$-$C_{12}$ alkyl, substituted or unsubstituted heteroatom-containing $C_1$-$C_{12}$ alkyl, substituted or unsubstituted $C_3$-$C_{12}$ cycloalkyl, and substituted or unsubstituted $C_3$-$C_{12}$ heteroatom-containing cycloalkyl. As a further example, $R^{10}$ is substituted or unsubstituted $C_1$-$C_{12}$ alkyl. For example, $R^{10}$ may be a branched $C_1$-$C_6$ alkyl chain.

In a preferred embodiment, $R^{10}$ is a secondary alkyl having the formula —CH($R^{11}$)($R^{12}$), where $R^{11}$ and $R^{12}$ are independently selected from lower alkyl. For example, $R^{11}$ and $R^{12}$ are independently methyl, ethyl, propyl, cyclopropyl, butyl, cyclobutyl, pentyl, cyclopentyl, hexyl, or cyclohexyl. In a preferred embodiment, $R^{11}$ is methyl and $R^{12}$ is cyclopropyl.

$R^{10}$ may be further substituted with one or more substituents selected from $C_1$-$C_{12}$ alkyl (including heteroatom-containing alkyl), $C_1$-$C_{12}$ alkenyl, $C_1$-$C_{12}$ alkynyl, $C_5$-$C_{24}$ aryl (including heteroaryl), $C_5$-$C_{24}$, $C_5$-$C_{24}$ alkaryl, $C_5$-$C_{24}$ aralkyl, and functional groups.

The preparative methods described herein provide large-scale preparation of the morphinans described herein. For example, in one embodiment, the disclosure provides a method for large scale preparation of a diastereomerically enriched morphinan.

The diastereomerically enriched morphinan products described herein may be prepared by a sequence of reaction steps using any appropriate starting material. In one embodiment, an appropriate starting material is an opioid. For example, the starting material may be selected from morphine, derivatives and/or analogs of morphine, and salts thereof such as sulfate salts.

In the process for forming a diastereomerically enriched morphinan, one or more hydroxyl groups may be protected using an appropriate hydroxyl protecting group. In one embodiment, an appropriate hydroxyl protecting group is an ester, and the one or more hydroxyl groups is converted to one or more ester groups via an esterification reaction, thus preparing an esterified product. In a preferred embodiment, two hydroxyl groups are converted to ester groups.

Any appropriate method for carrying out an esterification reaction may be used. Such methods may be found, for example, in J. March, *Advanced Organic Chemistry: Reactions, Mechanisms and Structure*, 5th Edition (New York: Wiley-Interscience, 2001). For example, the transesterification reaction involves reaction of one or more hydroxyl groups with an ester reactant under conditions effective to provide an esterified product. The ester reactant may be, for example, any appropriate ester such as methyl benzoate and the like. Alternatively, the hydroxyl groups may be reacted with an activated carbonyl compound. Activated carbonyl compounds are compounds containing a leaving group attached to a carbonyl group. Suitable activated carbonyl compounds include acid chlorides, acid bromides, and the like. For example, the activated carbonyl compound may be benzoyl chloride. Other hydroxyl protecting groups may be employed as appropriate.

Furthermore in the process of forming a diastereomerically enriched morphinan, an N-alkyl group such as an N-methyl group may be converted to an N—H group in a dealkylation reaction. For example, a demethylation reaction is a reaction that forms a demethylated product. Preferred dealkylation reactions are oxidative dealkylations. In one preferred embodiment, the dealkylation reaction is carried out using a mild oxidizing agent to convert the N-alkyl group to an aminal, followed by reaction with acid to convert the aminal to a secondary amine. By "mild oxidizing agent" is meant that the dealkylation reaction may be carried out using an oxidizing agent that is less oxidizing than permanganate salts. Examples of preferred oxidizing agents are azodicarboxylate compounds including methylazodicarboxylate, diethyl diazodicarboxylate (DEAD), di-isopropylazodicarboxyate, and the like. The aminal product may be converted to an amine via reaction with any appropriate acid such as, for example, mineral acids including hydrogen halides (e.g., HCl and HBr), sulfuric acid, and nitric acid, and carboxylic acids such as formic acid, acetic acid, and citric acid. The dealkylation reaction may also involve enzymatic dealkylation.

The dealkylation reaction may be carried out in any appropriate solvent such as those described herein infra. The dealkylation reaction is preferentially carried out under reaction conditions such that substantially complete reaction is obtained in less than 30 minutes, or less than 15 minutes, or less than 10 minutes, or less than 5 minutes. For example, reactions may be carried out using microwave heating instead of conductive heating methods (e.g., heating via a hot bath) to substantially reduce the amount of time required to complete the reaction.

In a preferred embodiment, the dealkylation reaction (including reaction with an acid), provides a dealkylated product in a yield of at least 50%, or at least 60%, or at least 65%, or at least 70%, or at least 80%, or at least 90%, or at least 95%, or at least 97% wherein yield is calculated based on the amount of starting material (e.g., morphine).

In preferred embodiments, the dealkylation does not involve toxic agents such as cyanic bromide, methyl chloroformate, or a-chloro ethyl chloroformate. Also preferably, the dealkylation reaction does not produce N—CN or N-carbamates as intermediates. Also preferably, the dealkylation reaction does not require workup using metals such as zinc.

Furthermore in the process of forming a diastereomerically enriched morphinan, an N—H group may be converted to an N-alkyl group via an N-alkylation reaction, to provide an N-alkylated product. In a preferred embodiment, the N-alkylation reaction is carried out via reductive amination of a carbonyl-containing compound. A mild reducing agent is preferred, such as sodium cyanoborohydride ($NaCNBH_3$). The carbonyl-containing compound may be, for example, a ketone or aldehydes. Where a ketone, the carbonyl-containing compound may be symmetric or asymmetric. In a preferred embodiment, the carbonyl-containing compound is an asymmetric ketone such as methylcyclopropylketone.

In a preferred embodiment, the N-alkylation reaction is carried out by combining a compound containing an N—H group (such as the dealkylated product described herein supra) with a carbonyl-containing compound to form a first solution, and adding a mild reducing agent to the first solution. The addition may be carried out, for example, dropwise or in portions. Prior to the addition, the reducing agent may be combined with additional carbonyl-containing compound to form a second solution. Furthermore, additional components may be present in either the first or the second solution. Such additional components include solvents, basic amines such as NEt$_3$, and acids such as acetic acid.

The N-alkylation reaction provides an N-alkylated product that may be a mixture of diastereomers, and the reaction will preferentially be substantially complete within 3 hours, or within 2 hours, or within 1 hour of beginning the addition of the reducing agent. Preferred N-alkylation methods according to the disclosure are able to provide the N-alkylated product in at least 60%, or at least 70%, or at least 80%, or at least 85% yield (calculated based on the amount of the compound containing an N—H group used).

Furthermore in the process of forming a diastereomerically enriched morphinan, the N-alkylated product is purified in a purification step. The purification step is able to provide a diastereomerically enriched N-alkylated product by separating diastereomers in a mixture. In a preferred embodiment, the purification step involves crystallization. Purification by crystallization may involve the use of a resolving agent to form a salt with the desired diastereomer. A preferred resolving agent is 1-R-(+)-3-bromocamphor-8-sulphonic acid (1-R-BCS) and salts thereof (such as, for example, the ammonium salt). After the salt of the diastereomerically enriched N-alkylated product is crystallized and isolated, the salt formed with the resolving agent may be converted to the free base using, for example, dilute NH$_4$OH. Furthermore, the mother liquor from the crystallizations may be further concentrated or otherwise processed (e.g., recrystallized) to increase the yield of diastereomerically enriched N-alkylated product.

In a preferred embodiment, the purification step is suitable for large-scale purification. Also in preferred embodiments, the purification step is other than a chromatography method such as HPLC, and other than fractional crystallization.

The yield of diastereomerically enriched morphinan may be further enhanced by epimerizing the diastereomer that is not isolated in the purification method described above. For example, the undesired diastereomer can be epimerized by heating the compound in a high-boiling solvent. In a preferred embodiment, an acid salt of the hydroxy-protected form of the desired morphinan compound is dissolved in a high-boiling solvent and heated to reflux until the undesired diastereomer has epimerized to form about a 50/50 mixture of diastereomers.

Any high boiling solvent can be used for the epimerization reaction. Solvents include, for example, dichloroethane, as well as polar solvents such as DMF, Cyclohexanone, ethers, and the like.

Furthermore in the process of forming a diastereomerically enriched morphinan, the one or more hydroxyl groups protected using hydroxyl protecting groups (see discussion supra) may be deprotected in a hydroxyl-deprotection reaction. The hydroxyl-deprotection reaction may be any appropriate method for removing hydroxyl protecting groups. In a preferred method, the hydroxyl-deprotection reaction involves treatment of the compound comprising protected hydroxyl groups with a base (e.g., sodium salts such as NaOH and the like) in a solvent (e.g., alcohols such as methanol and the like).

In preferred embodiments of the methods described herein, a diastereomerically enriched morphinan may be prepared on a large scale, for example on an industrial production scale rather than on a experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of diastereomerically enriched morphinan. The methods allow such preparations in an amount of time that is less than 3 days, or less than 2 days, or less than 1 day. Furthermore, the methods allow the preparation of a diastereomerically enriched morphinan from the starting material in about four reaction steps. Furthermore, the methods allow the preparation of a diastereomerically enriched morphinan from a starting material as described herein in about 30% yield, or about 25% yield, and having a diastereomeric enrichment of at least 90%, or at least 95%, or at least 98%.

For example, in the Example provided below, diastereomerically enriched PPL-101 is prepared in four reaction steps (i.e., protection of the hydroxyl groups, N-dealkylation, N-alkylation, deprotection of the hydroxyl groups), and in 37% overall yield from morphine.

It will be appreciated that any of the reactions described herein may be carried out in an appropriate solvent. Furthermore, where energy is required, such energy may be delivered via any appropriate method. For example, energy may be delivered via submersion in a hot bath or irradiation using microwaves.

It will be appreciated that the methods disclosed herein are also suitable for small-scale preparations of the desired compounds.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

As shown in Scheme 1, commercially available Morphine (or Morphine sulfate converted to the free base form) is converted to the bis-3,6-benzoate ester 3 by heating at 70° C. in pyridine/dichloroethane with 3.3 equivalents of benzoyl chloride.

The resulting Morphine-3,6-dibenzoate (3) was subjected to an N-demethylation step using methylazodicarboxylate as a mild oxidizing agent and di-isopropylazodicarboxylate (DIAD) to convert the N-methyl to an aminal. Using microwaves to accelerate the process, the entire process was complete in 3 minutes.

Simple exposure of the aminal to 1 N HCl in THF completed the formation of 4 in near quantitative yield. The overall yield from morphine to Normorphine-3,6-dibenzoate ester (4) was 67%.

Scheme 1.

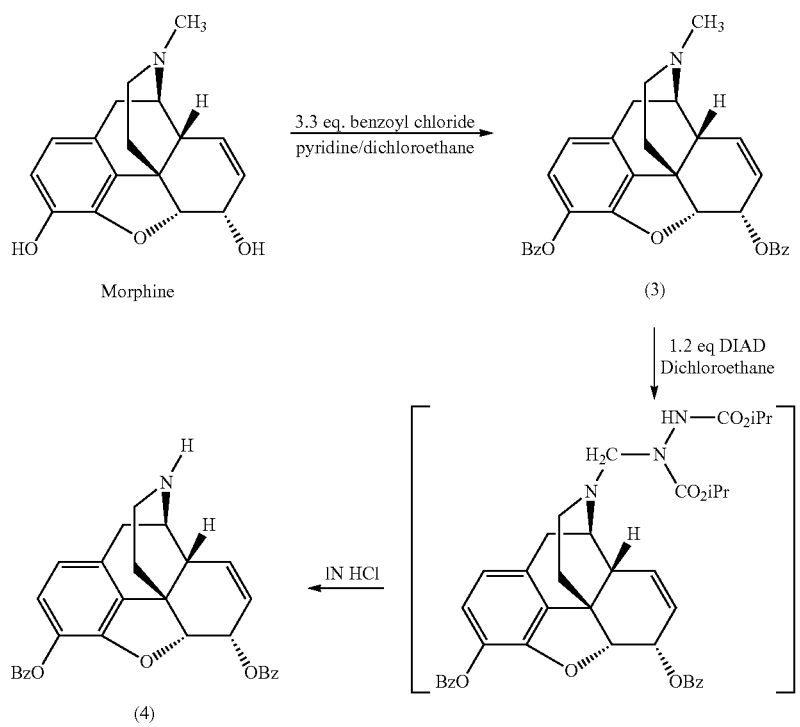

As shown in Scheme 2, 4 N solution of sodium cyanoborohydride in commercial methylcyclopropylketone was prepared. Then a stirred solution of (4) in methylcyclopropylketone with 2 eq. of NEt₃ and 2 eq. of acetic acid at 70° C. was treated dropwise with the 4 N sodium cyanoborohydride solution; the desired product (5) was formed in 60 minutes. After workup, the dibenzoate ester of PPL-101 and its diastereomer were recovered in 87% yield.

Scheme 2.

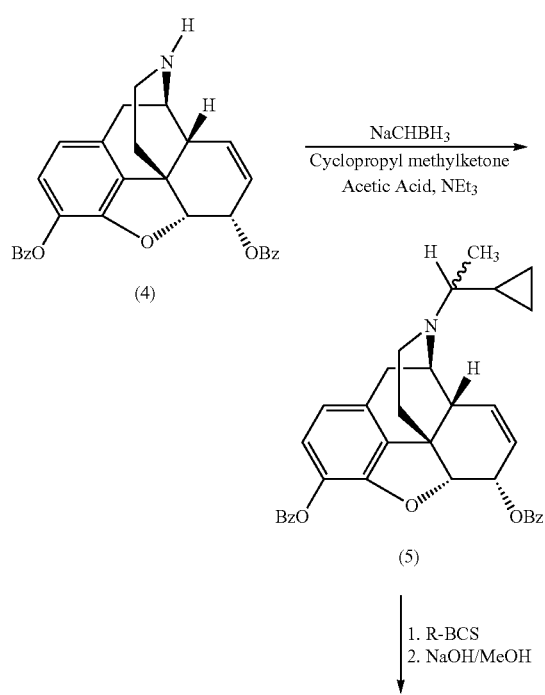

-continued

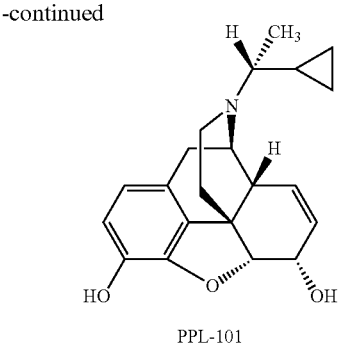

PPL-101

Without further purification, 4.99 g of 5 (9.1 mmoles) of the mixture of diastereomers (5) were dissolved in 100 mL of isopropanol and treated with 4N HCl in dioxane to pH=4. Then, 0.5 eq of 1-R-(+)-3-bromocamphor-8-sulphonic acid ammonium salt (R-BCS, 4.4 mmoles, 1.43 g) as a solution in 5.0 mL H₂O at 60° C. was added in one portion with stirring. After 1 minute, microcrystals appeared. Crop 1 was collected by filtration: 2.69 g, 64% yield (assuming 50:50 ratio of diastereomers). Evaporation of the liquors provides a second crop, wt 1.78 g. Total weight: 4.47 g, 5.2 mmoles, crude yield=114%.

Treatment of a slurry of 1-R-BCS salt of (5) in water with dilute NH₄OH released the free base, which was extracted into ether to afford a colorless glass, wt=2.27 g, 92% yield. Treatment of the product with NaOH in methanol rapidly removes the esters. The solution was adjusted to pH 7 with dilute HCl, and PPL-101 is extracted from the aqueous layer with dichloromethane in 95% yield. NMR was used to confirm the identity of PPL-101 and to show that the other diastereomer was not present.

The unwanted S-diastereomer from the preparation of PPL-101 is epimerized to the desired R-epimer, PPL-101, allowing further improvement in overall product yield. Thus, 100 mg of the S-diastereomer of PPL-101 as the dibenzoate diester, as the HCl salt, was heated in 1,2-dichoroethane at reflux until TLC showed that the pure starting material was two equal spots of the S- and R-diastereomers of PPL-101 dibenzoate ester. This process can be carried out in a sealed reaction vessel at 100° C., shortening the reaction time to 6 hours. Subsequently, the mixture of isomers was again purified to the single desired R-diastereomer, as described previously, with structures confirmed by NMR.

What is claimed is:

1. A method for preparing a diastereomerically enriched morphinan comprising: (a) providing morphine or an analog thereof; (b) converting one or more hydroxyl groups on the morphine to one or more ester groups, in an esterification reaction, to prepare an esterified product; (c) converting the N-methyl group on the esterified product to an N—H group, in a demethylation reaction, to prepare a demethylated product, using a demethylation reagent comprising a mild oxidizing agent; (d) converting the N—H group on the demethylated product to an N-alkyl group, in an alkylation reaction, to prepare an alkylated product; and (e) purifying the alkylated product in a purification step, wherein the morphinan has the structure of formula (Ia)

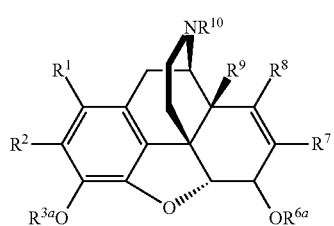

wherein, in formula (Ia):
$R^1$ and $R^2$ and $R^7$ to $R^9$ are H;
$R^{10}$ is an alkyl having the formula —CH$(R^{11})(R^{12})$, where $R^{11}$ and $R^{12}$ are independently methyl, ethyl, propyl, cyclopropyl, butyl, cyclobutyl, pentyl, cyclopentyl, hexyl, or cyclohexyl; and
$R^{3a}$ and $R^{6a}$ are independently selected from H, substituted or unsubstituted $C_1$-$C_{12}$ alkyl, and hydroxyl protecting groups.

2. The method of claim 1, wherein the morphinan has the structure of formula (Ib)

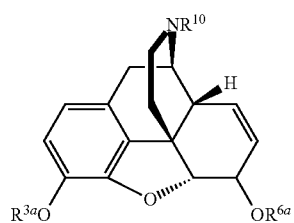

wherein, in formula (Ib):
$R^{3a}$ and $R^{6a}$ are hydrogen or hydroxyl protecting groups; and
$R^{10}$ is selected from substituted or unsubstituted $C_1$-$C_{12}$ alkyl, substituted or unsubstituted heteroatom-containing $C_1$-$C_{12}$ alkyl, substituted or unsubstituted $C_3$-$C_{12}$ cycloalkyl, and substituted or unsubstituted $C_3$-$C_{12}$ heteroatom-containing cycloalkyl.

3. The method of claim 2, wherein $R^{10}$ is substituted or unsubstituted $C_1$-$C_{12}$ alkyl.

4. The method of claim 3, wherein the morphinan has the structure

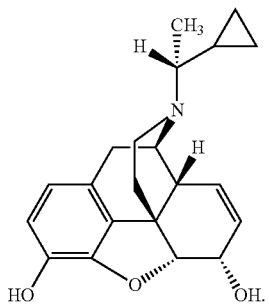 [SMILES: C[C@H](C1CC1)N1CC[C@]23c4c5ccc(O)c4O[C@H]2[C@@H](O)C=C[C@H]3[C@H]1C5]

5. The method of claim 1, wherein the esterification reaction converts two hydroxyl groups to benzoate groups.

6. The method of claim 1, wherein the demethylation reaction comprises contacting the esterified product with di-iso-propylazodicarboxylate in the presence of microwaves.

7. The method of claim 6, wherein the demethylation reaction reaches at least 70% completion within about 30 minutes.

8. The method of claim 1, wherein the alkylation reaction comprises contacting the demethylated product with NaCNBH$_3$ and methylcyclopropylketone, and wherein the alkylated product comprises an α-methyl-cyclopropyl-methyl group.

9. The method of claim 1, wherein the purification step comprises contacting the alkylated product with a resolving agent to form a salt.

10. The method of claim 9, wherein the resolving agent is 1-R-(+)-3-bromocamphor-8-sulphonic acid ammonium salt.

11. The method of claim 9, further comprising: (a) recrystallizing the salt to provide crystals; (b) optionally contacting the crystals with a reagent effective to remove the resolving agent and provide an esterified morphinan; and (c) optionally contacting the esterified morphinan with a reagent effective to convert the one or more ester groups to one or more hydroxyl groups and provide the diastereomerically enriched morphinan.

12. The method of claim 1, wherein the diastereomerically enriched morphinan is produced in at least 25% yield from the morphine or analog thereof.

13. The method of claim 1, wherein the diastereomerically enriched morphinan has an diastereomeric enrichment of at least 90%.

14. The method of claim 1, wherein the diastereomerically enriched morphinan is produced on a large scale.

15. The method of claim 14, wherein the method is carried out in a batch-type process over a period of time, and wherein the batch-type process produces an amount of the diastereomerically enriched morphinan.

16. The method of claim 15, wherein the amount of diastereomerically enriched morphinan is at least 10 g.

17. The method of claim 15, wherein the period of time is less than 3 days.

18. A method for preparing a diastereomerically enriched morphinan, the comprising contacting a diasteriomeric mixture of the morphinan with a resolving agent to form a salt and selectively recrystallizing one of the morphinan diastereoisomers, wherein the morphinan has the structure of formula (Ia)

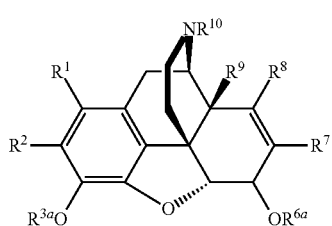

(Ia)

wherein, in formula (Ia):
$R^1$ and $R^2$ and $R^7$ to $R^9$ are H;
$R^{10}$ is an alkyl having the formula —CH $(R^{11})(R^{12})$, where $R^{11}$ and $R^{12}$ are independently methyl, ethyl, propyl, cyclopropyl, butyl, cyclobutyl, pentyl, cyclopentyl, hexyl, or cyclohexyl; and
$R^{3a}$ and $R^{6a}$ are independently selected from H, substituted or unsubstituted $C_1$-$C_{12}$ alkyl, and hydroxyl protecting groups.

19. The method of claim 18, wherein the morphinan has the structure

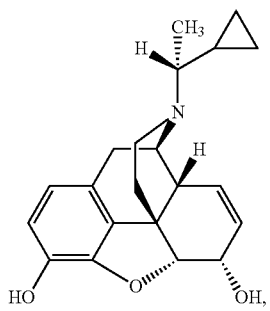 [SMILES: C[C@H](C1CC1)N1CC[C@]23c4c5ccc(O)c4O[C@H]2[C@@H](O)C=C[C@H]3[C@H]1C5]

and wherein the (R)-isomer is selectively recrystallized.

20. The method of claim 18, wherein the resolving agent is 1-R-(+)-3-bromocamphor-8-sulphonic acid ammonium salt.

21. A method for preparing a diastereomerically enriched morphinan, comprising: (a) providing a mixture of the diastereomers of a morphinan; (b) epimerizing one of the diastereomers of the morphinan; (c) contacting the result from (b) with a resolving agent; and (d) recrystallizing the result from (c); wherein the morphinan has the structure of formula (Ia)

(Ia)

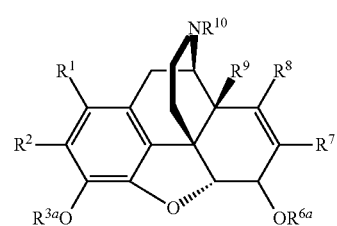

wherein, in formula (Ia):
$R^1$ and $R^2$ and $R^7$ to $R^9$ are H;
$R^{10}$ is an alkyl having the formula —CH $(R^{11})(R^{12})$, where $R^{11}$ and $R^{12}$ are independently methyl, ethyl, propyl, cyclopropyl, butyl, cyclobutyl, pentyl, cyclopentyl, hexyl, or cyclohexyl; and
$R^{3a}$ and $R^{6a}$ are independently selected from H, substituted or unsubstituted $C_1$-$C_{12}$ alkyl, and hydroxyl protecting groups.

22. The method of claim 21, wherein the morphinan has the structure

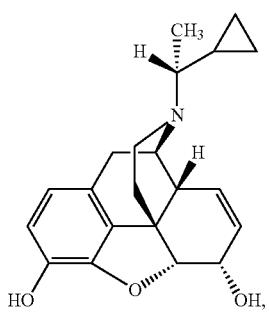

and wherein the (S)-diastereomer is epimerized to the (R)-diastereomer.

23. The method of claim 21, wherein the resolving agent is 1-R-(+)-3-bromocamphor-8-sulphonic acid ammonium salt.

24. A method for preparing a morphinan, comprising contacting a diester derivative of morphine with a demethylation reagent under reaction conditions effective to N-demethylate the diester derivative of morphine, wherein the demethylation reagent is a mild oxidizing agent, and wherein the morphinan has the structure of formula (Ia)

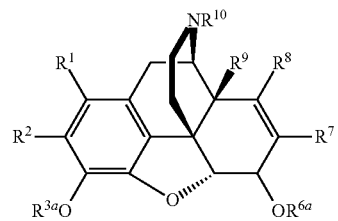

(Ia)

wherein, in formula (Ia):
$R^1$ and $R^2$ and $R^7$ to $R^9$ are H;
$R^{10}$ is an alkyl having the formula —CH $(R^{11})(R^{12})$, where $R^{11}$ and $R^{12}$ are independently methyl, ethyl, propyl, cyclopropyl, butyl, cyclobutyl, pentyl, cyclopentyl, hexyl, or cyclohexyl; and
$R^{3a}$ and $R^{6a}$ are independently selected from H, substituted or unsubstituted $C_1$-$C_{12}$ alkyl, and hydroxyl protecting groups.

25. The method of claim 24, wherein the morphinan has the structure

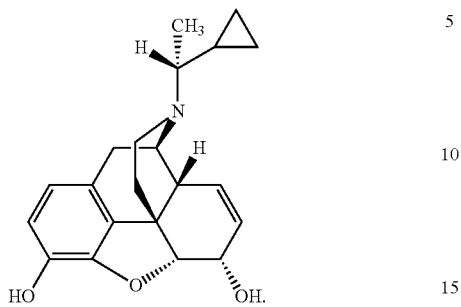

26. The method of claim 25, wherein the diester derivative is the dibenzoate derivative.

27. The method of claim 24, wherein the method further comprises: (a) alkylating the N-demethylated diester derivative of morphine; and (b) purifying the product from (a) in a purification step.

28. The method of claim 27, wherein the purification step is a method for separation of diastereomers other than chromatography.

29. The method of claim 28, wherein the purification step involves crystallization.

30. The method of claim 2, wherein $R^{3a}$ and $R^{6a}$ are H and $R^{10}$ is substituted $C_1$-$C_{12}$ alkyl.

* * * * *